(12) United States Patent
Morin et al.

(10) Patent No.: US 11,534,296 B2
(45) Date of Patent: Dec. 27, 2022

(54) FOLDING PATTERNS AND LOADING FUNNEL FOR IMPROVED TRANSCATHETER VALVE LOADING FORCES

(71) Applicant: St. Jude Medical, Cardiology Division, Inc., St. Paul, MN (US)

(72) Inventors: Kristen T. Morin, St. Paul, MN (US); Keith High, White Bear Lake, MN (US); Ian Wright, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 463 days.

(21) Appl. No.: 16/748,082

(22) Filed: Jan. 21, 2020

(65) Prior Publication Data

US 2020/0170792 A1 Jun. 4, 2020

Related U.S. Application Data

(62) Division of application No. 16/166,687, filed on Oct. 22, 2018, now Pat. No. 10,575,949.

(60) Provisional application No. 62/575,695, filed on Oct. 23, 2017.

(51) Int. Cl.
*A61F 2/24* (2006.01)
*A61F 2/95* (2013.01)

(52) U.S. Cl.
CPC .......... *A61F 2/2427* (2013.01); *A61F 2/2412* (2013.01); *A61F 2/2418* (2013.01); *A61F 2/9522* (2020.05); *A61F 2/9525* (2020.05)

(58) Field of Classification Search
CPC ........ A61F 2/24; A61F 2/2412; A61F 2/2418; A61F 2/2427; A61F 2/95; A61F 2/9522; A61F 2/9525
See application file for complete search history.

(56) References Cited

U.S. PATENT DOCUMENTS

| | | | |
|---|---|---|---|
| 9,492,274 B2 * | 11/2016 | Johnson | A61F 2/2427 |
| 9,642,703 B2 * | 5/2017 | Hillukka | A61F 2/2436 |
| 10,010,412 B2 | 7/2018 | Taft et al. | |
| 10,335,270 B2 | 7/2019 | Essinger et al. | |
| 10,368,986 B2 * | 8/2019 | Gosal | A61F 2/9525 |
| 10,441,412 B2 * | 10/2019 | Quadri | A61F 2/2418 |
| 10,874,512 B2 * | 12/2020 | von Oepen | A61F 2/2436 |
| 2010/0101682 A1 | 4/2010 | Barber et al. | |
| 2012/0330408 A1 * | 12/2012 | Hillukka | A61F 2/2427 623/2.11 |

(Continued)

*Primary Examiner* — Nguyen Q. Ha
(74) *Attorney, Agent, or Firm* — Wei & Sleman LLP

(57) ABSTRACT

A loading assembly for crimping and loading a prosthetic heart valve into a delivery device includes a loading base, a base funnel, and a compression member. The loading base has a support and a body extending from the support with a recess defined within the body. The recess is configured to receive a substantial portion of the annulus section of the heart valve in an at least partially collapsed condition. The base funnel is configured to be coupled to the loading base and to at least partially collapse the annulus section of the heart valve as it is inserted into the recess in the loading base. The compression member is configured to be coupled to the loading base with the heart valve inserted in the recess for further collapsing the heart valve and loading it into the delivery device.

8 Claims, 14 Drawing Sheets

(56) References Cited

U.S. PATENT DOCUMENTS

| | | | |
|---|---|---|---|
| 2013/0166020 A1* | 6/2013 | Hillukka | A61F 2/9525 623/2.11 |
| 2014/0331475 A1 | 11/2014 | Duffy et al. | |
| 2019/0117394 A1 | 4/2019 | Morin et al. | |

* cited by examiner

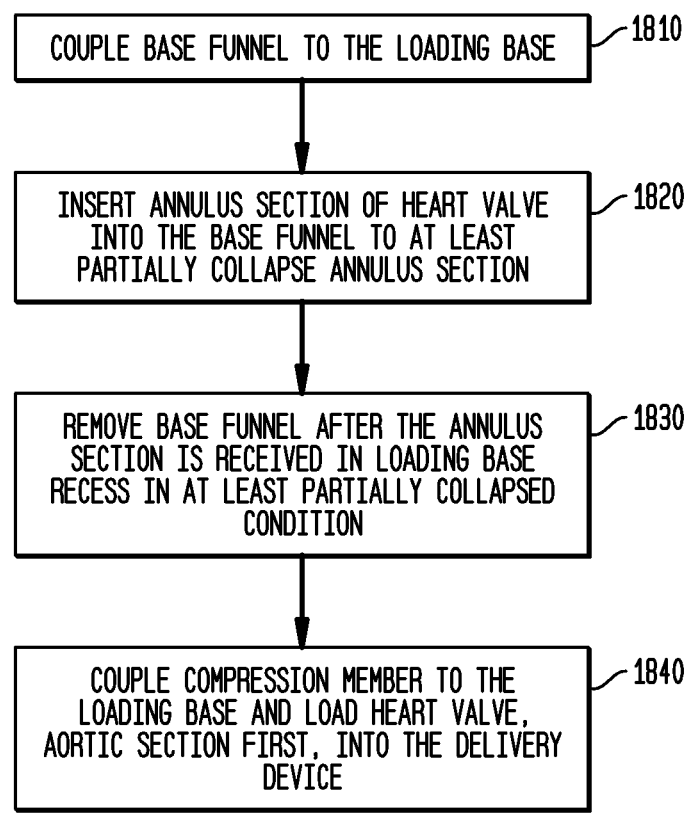

FOLDING PATTERNS AND LOADING
FUNNEL FOR IMPROVED
TRANSCATHETER VALVE LOADING
FORCES

CROSS-REFERENCE TO RELATED
APPLICATION

The present application is a divisional of U.S. patent application Ser. No. 16/166,687, filed on Oct. 22, 2018, which claims the benefit of the filing date of U.S. Provisional Patent Application No. 62/575,695 filed Oct. 23, 2017, all of which are incorporated herein by reference.

BACKGROUND OF THE INVENTION

The present disclosure relates to prosthetic heart valve implantation and, more particularly, to assemblies and methods for loading a self-expanding collapsible heart valve into a delivery device.

Prosthetic heart valves may be formed from biological materials such as harvested bovine valves or pericardium tissue. Such valves are typically fitted within a stent, which may be inserted into the heart at the annulus of the compromised native valve to replace the native valve. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. To perform such insertion procedure, it is often necessary to compress the stent to a reduced diameter for loading into the delivery device.

In the case of prosthetic valves formed from biological materials, the stented valve is preferably preserved in the open condition for storage. The valve may be crimped or its diameter be reduced for loading in the delivery device, in the operating arena.

Present devices and methods for collapsing a stented valve having an outer cuff may require high forces to load the collapsed valve into the delivery device due to the larger collapsed size of the valve. Additionally, the outer cuff of the valve may have a tendency to catch on an edge of the delivery device. It would therefore be beneficial to provide different devices and methods for collapsing a stented heart valve using apparatus and techniques. Such devices and methods would allow for a successful and efficient loading of the heart valve in the delivery device.

BRIEF SUMMARY OF THE INVENTION

According to an embodiment of the disclosure, a compression member for collapsing a prosthetic heart valve comprises a first open end with a first diameter, a second open end with a second diameter smaller than the first diameter, a tapered wall decreasing in diameter from the first open end to the second open end and having an inner surface, the tapered wall defining an open space adapted to receive the prosthetic heart valve, and a plurality of protrusions on the inner surface of the tapered wall, the protrusions being adapted to urge portions of an outer cuff of the prosthetic heart valve to an interior of the valve as the valve moves from the first open end toward the second open end.

According to an embodiment of the disclosure, a system for collapsing a prosthetic heart valve comprises a loading base having a body and a recess formed in the body, the recess having a support surface and being configured to receive an annulus section of a prosthetic valve in an at least partially collapsed condition, a first compression member having a first open end with a first diameter, a second open end with a second diameter smaller than the first diameter, and a tapered wall decreasing in diameter from the first open end to the second open end, and a second compression member having a first open end with a third diameter, a tubular extension at the first open end, a second open end with a fourth diameter larger than the third diameter, and a tapered wall decreasing in diameter from the second open end to the tubular extension. The first compression member is configured to be positioned against the loading base, to receive the annulus section of the prosthetic valve in an expanded condition and to collapse the annulus section of the prosthetic valve to the at least partially collapsed condition. The second compression member is configured to be positioned against the loading base at the second open end and to collapse an aortic section and the at least partially collapsed annulus section of the prosthetic valve.

According to an aspect of the disclosure, a method for loading a prosthetic heart valve into a delivery device comprises at least partially collapsing an annulus section of the prosthetic heart valve by inserting through an orifice, positioning the at least partially collapsed annulus section in a loading base, collapsing an aortic section of the prosthetic heart valve, and loading the collapsed aortic section into the delivery device.

BRIEF DESCRIPTION OF THE DRAWINGS

Various embodiments of the present loading assembly are disclosed herein with reference to the drawings, wherein:

FIG. 17 is a flow chart of a method for loading a prosthetic heart valve into a delivery device using the loading base of FIG. 15A and the base funnel of FIG. 15B.

DETAILED DESCRIPTION

Figure 1:
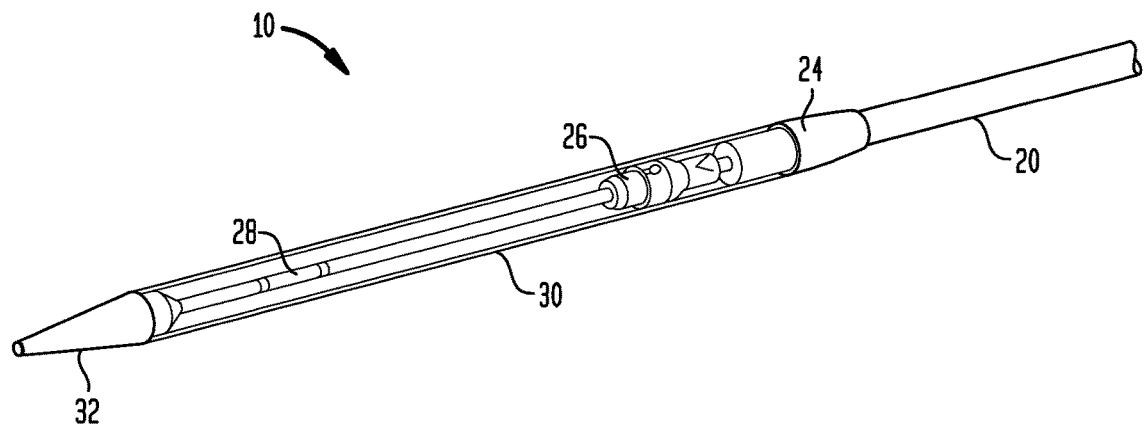
FIG. 1 is a perspective view of a distal portion of a prior art delivery device.

Embodiments of the presently disclosed loading assemblies and heart valves are described herein in detail with reference to the drawing figures, wherein like reference numerals identify similar or identical elements. In the drawings and in the description which follows, the term "proximal" refers to the end of the loading assembly, or portion thereof, which is closest to the operator during use, while the term "distal" refers to the end of the loading assembly, or portion thereof, which is farthest from the operator during use.

The present disclosure relates to assemblies and methods for loading a self-expanding stent or a collapsible prosthetic heart valve into a minimally invasive delivery device. An exemplary minimally invasive delivery device 10 is illustrated in FIGS. 1 and 2.

Figure 2:
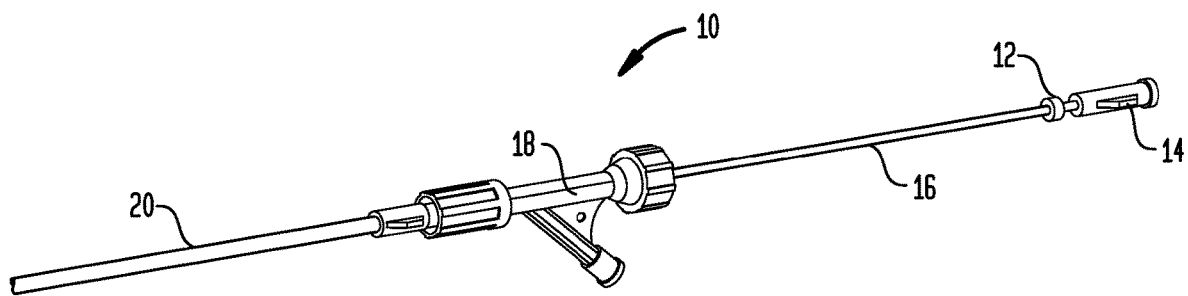
FIG. 2 is a perspective view of a proximal portion of the delivery device of FIG. 1.

As seen in FIG. 2, the delivery device 10 may include an inner tube 16 having a lumen extending therethrough. A hub 14 is mounted on the proximal end of the inner tube 16 and is adapted for connection to another system or mechanism, such as a handle, a syringe or a mechanism for displacing a distal sheath 30. Mechanisms for displacing the distal sheath 30 are described in International Patent Application Publication No. WO/2009/091509, the entire contents of which are hereby incorporated herein by reference. A retention ring 12 may also be mounted on the proximal end of the inner tube 16.

As shown in FIG. 1, an outer shaft 20 of the delivery device 10 extends to a transition member 24, which may have a tapered shape. The transition member 24 interconnects a distal end of the outer shaft 20 and the distal sheath 30. The distal sheath 30 surrounds a retaining element 26 and a support shaft 28 and can maintain a prosthetic heart valve mounted around the support shaft in a collapsed condition. The support shaft 28 is operatively connected to the inner tube 16 and has a lumen extending therethrough for receiving a guidewire (not shown). The retaining element 26 is mounted on the support shaft 28 and is configured for supporting an end of a prosthetic heart valve or any other suitable medical implant. The retaining element 26 may be longitudinally and rotatably fixed relative to the support shaft 28, thereby preventing the cells of the stent from entangling with one another during deployment. The distal sheath 30 covers the retaining element 26 and at least a portion of the support shaft 28 and is movable relative to the support shaft between a distal position shown in FIG. 1 and a proximal position (not shown). An atraumatic tip 32 may be connected to the distal end of the support shaft 28, and may have a tapered shape.

Figure 3:
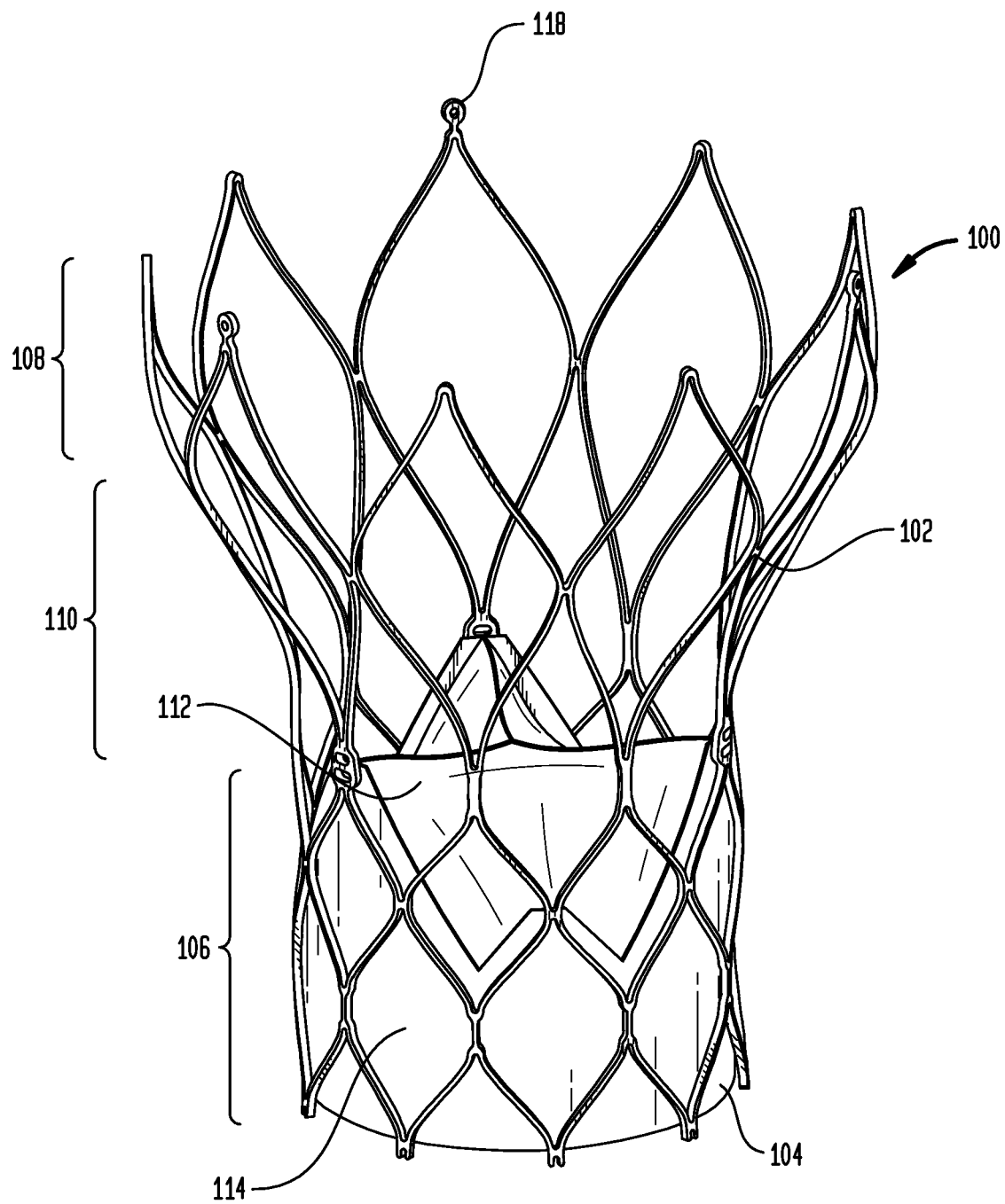
FIG. 3 is a perspective view of a prior art embodiment of a collapsible prosthetic heart valve in an expanded condition.

FIG. 3 shows one embodiment of a prosthetic valve 100 designed to replace a native aortic valve. The valve 100 has a collapsed condition and an expanded condition and may be formed from a collapsible framework or stent 102, with a valve assembly 104 internally connected to the stent. The stent 102 may be formed from any suitable biocompatible material, such as nitinol, and may include an annulus section 106, an aortic section 108, and an intermediate section 110. The aortic section 108 may have a larger diameter than the annulus section 106 in the expanded condition. The intermediate section 110 of the stent 102 is located between the annulus section 106 and the aortic section 108. The valve assembly 104 may include a plurality of leaflets 112 and an inner cuff 114 attached to the stent 102. The leaflets 112 and the inner cuff 114 may be formed from a biocompatible polymer, from bovine or porcine pericardial tissue, or from other appropriate biocompatible materials. The valve assembly 104 is connected to the stent 102 generally within the annulus section 106, but may extend into the intermediate section 110. The valve 100 may include tabs or retaining members 118 at spaced positions around one or both ends of the stent 102. The retaining members 118 are typically designed to mate with pockets (not shown) in retaining element 26 to maintain the prosthetic valve 100 in assembled relationship with the delivery device 10, to minimize longitudinal movement of the prosthetic valve relative to the delivery device during unsheathing and resheathing procedures, to help prevent rotation of the prosthetic valve relative to the delivery device as the delivery device is advanced to the target site and during deployment, and to maintain the alignment of the stent cells and prevent them from becoming tangled.

Figure 4:
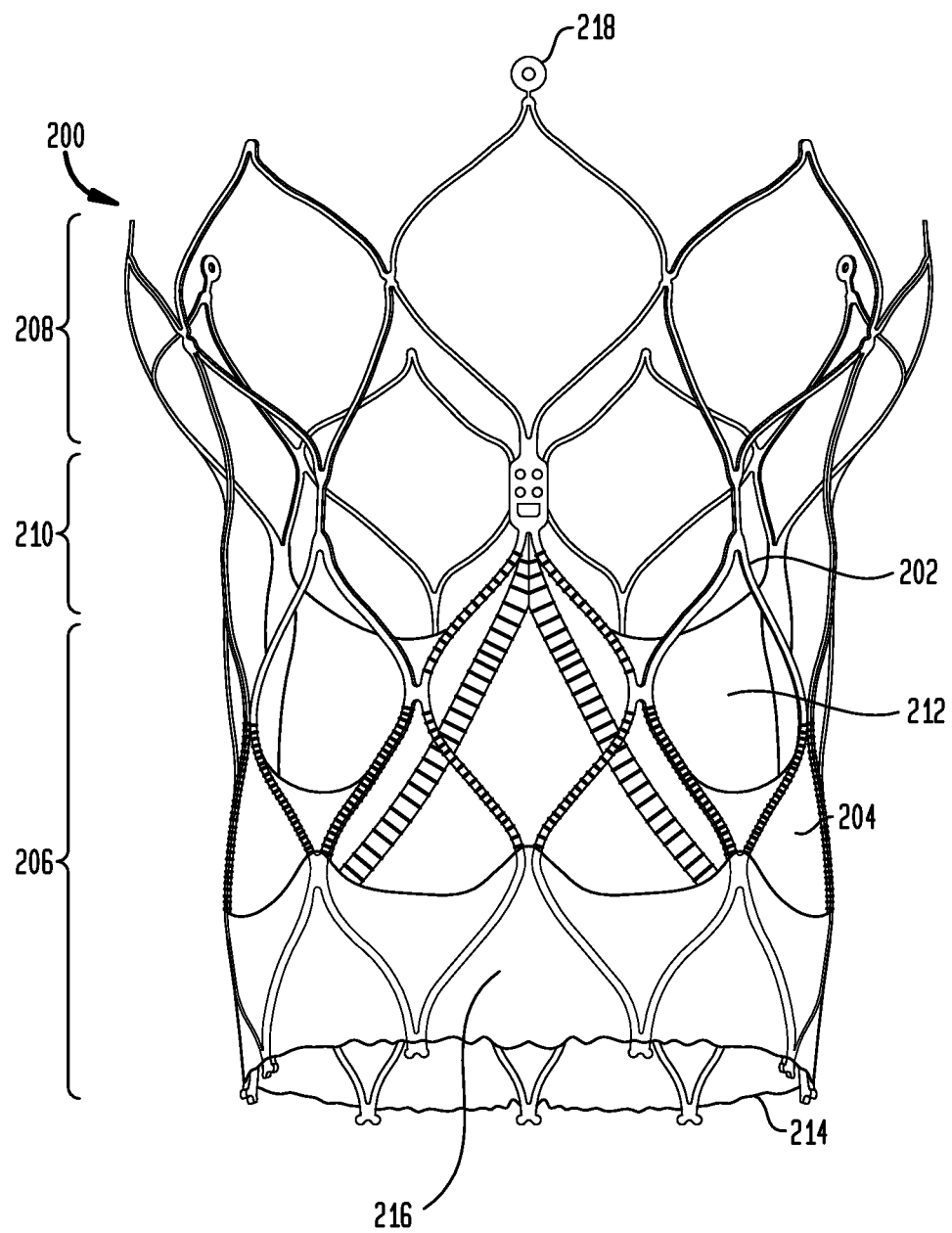
FIG. 4 is a front view of another embodiment of a collapsible prosthetic heart valve in an expanded condition.

FIG. 4 shows another embodiment of a prosthetic valve 200 designed to replace a native aortic valve. The valve 200 may be similar in construction to the valve 100 described above and may be formed from a collapsible framework or stent 202, with a valve assembly 204 internally connected to the stent. The stent 202 may include an annulus section 206, an aortic section 208, and an intermediate section 210. The aortic section 208 may have a larger diameter than the annulus section 206 in the expanded condition. The intermediate section 210 of the stent 202 is located between the annulus section 206 and the aortic section 208. The valve assembly 204 may include a plurality of leaflets 212 and an inner cuff 214 attached to the stent 202. The valve 200 further includes an outer cuff 216 attached to the annulus section 206. More examples of outer cuffs are described in U.S. Pat. No. 8,808,356, the entire content of which is hereby incorporated herein by reference. The outer cuff 216 promotes sealing with native tissue even where the native tissue is irregular.

The prosthetic valves 100, 200 are preferably stored in their expanded or open condition. As such, the valves 100, 200 may be crimped into a collapsed or reduced diameter condition for surgical implantation. The crimping process is preferably conducted in the operating arena by the surgeon, interventional cardiologist or surgical assistant using a specialized assembly.

Figure 5:
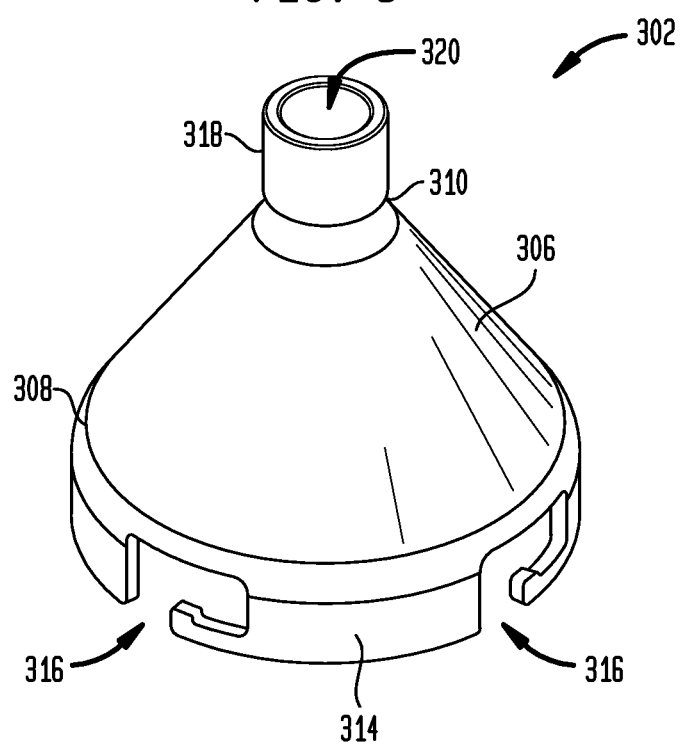
FIG. 5 is a perspective view of a loading funnel.
Figure 6:
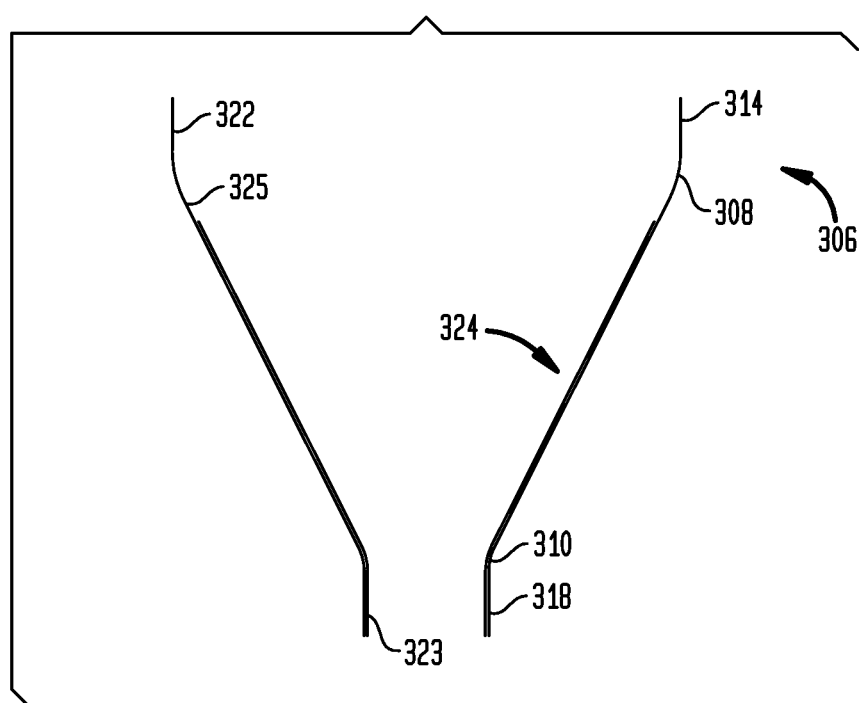
FIG. 6 is a schematic longitudinal cross-section of the loading funnel of FIG. 5, illustrating a coating applied to the inner surface thereof.
Figure 7:
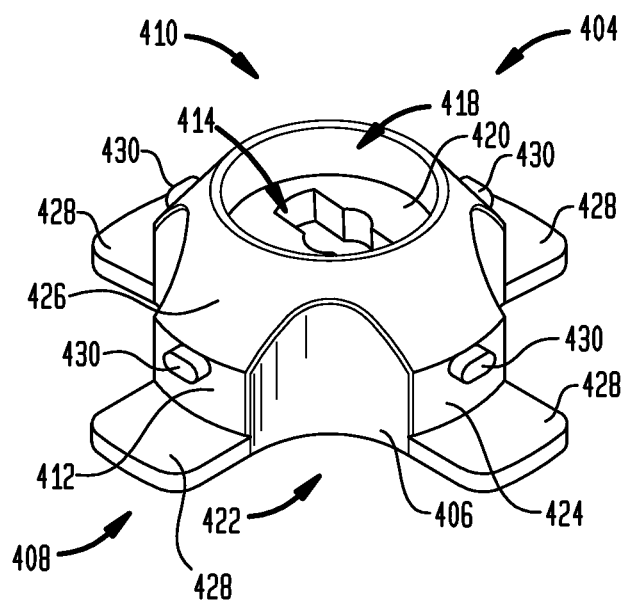
FIG. 7 is a perspective view of a loading base for use with the loading funnel of FIG. 5.

Some exemplary loading assemblies for loading the prosthetic valve 200 into a delivery device are described in U.S. Pat. Nos. 9,021,674; 8,931,159; and 8,893,370, the entire contents of which are hereby incorporated herein by reference. Referring now to FIGS. 5-7, a loading assembly according to an embodiment of the present invention is illustrated. The loading assembly generally includes a compression member 302 and a loading base 404, both adapted to be coupled to one another. The compression member 302 includes a funnel 306 having a substantially frusto-conical shape with a larger diameter at a first end 308 and a smaller diameter at a second end 310. The diameter of the funnel 306 may decrease either uniformly or non-uniformly from the first end 308 to the second end 310 to compress the valve 200 as the valve is advanced through the compression member 302. The compression member 302 is preferably made of a substantially rigid material, and may be wholly or partly made of a transparent plastic, such as polycarbonate or acrylic, to allow viewing of the valve 200 during loading.

The compression member 302 may further include an annular rim 314 extending from the first end 308 of the funnel 306 for joining the compression member to the loading base 404 as described below. The rim 314 may include a plurality of slots 316 disposed around its outer periphery. While the drawings show slots 316 that are substantially P-shaped, the slots may have any other shapes suitable for securely holding the compression member 302 to the loading base 404. The rim 314 may include four such slots 316, or more or less than four. Regardless of the number or slots 316, adjacent slots are preferably spaced equidistantly from each other.

The compression member 302 also may include a tubular extension 318 projecting from the second end 310 of the funnel 306. The tubular extension 318 has an opening 320 therethrough in communication with the interior of funnel 306. The opening 320 is sized and shaped to receive the distal sheath 30 of the delivery device 10 therein. The cross-section of the tubular extension 318 is preferably substantially circular, but may be oblong, oval, elliptical, or polygonal.

FIG. 6 depicts a schematic longitudinal cross-section of the compression member 302, showing the inner surface 322 thereof. In an exemplary embodiment, at least a portion of the inner surface 322 is coated with a layer 324 of a hydrophilic coating (HPC). By way of non-limiting examples, the HPC may include lubricious coatings available under the trade mark Serene™ from Surmodics, Inc. of Eden Prairie, Minn. The layer 324 serves to reduce friction between the inner surface 322 and the valve 200, including the stent 202 and the outer cuff 216.

In one embodiment, the entire inner surface 322 of the compression member 302 may be coated with the layer 324 of the HPC. In another embodiment, only those portions of the inner surface 322 of the compression member 302 that are envisioned to contact the valve 200 are coated with the layer 324 of the HPC. For instance, the entire inner surface 323 of the tubular extension 318 is likely to contact the valve 200 and therefore may be coated with the HPC layer 324. Likewise, the inner surface 325 of funnel 306 between the first end 308 and the second end 310 is likely to contact the valve 200 and may be coated entirely with the HPC layer 324.

In an example, the HPC layer 324 may have a thickness ranging from about 500 nanometers (nm) to about 5 micron (μm). In one example, the HPC layer 324 may have a uniform thickness along the inner surface 322. In another embodiment, the HPC layer 324 may have varying thicknesses along the inner surface 322. For instance, the thickness of the HPC layer 324 may be at a minimum proximal to the first end 308 of funnel 306 and may increase to a maximum towards the second end 310 of the funnel. In addition or alternatively, the HPC layer 324 may be thicker on the inner surface 323 of tubular extension 318 than on the inner surface 325 of funnel 306.

The HPC layer 324 may be applied to the inner surface 322 of the compression member 302 using any known technique, such as dip coating, spray coating, film coating, chemical vapor deposition or silk screening. To facilitate dip coating, for example, the outer surface of the compression member 302 may be also be coated with an HPC layer. Once the HPC layer 324 has been applied to the inner surface 322, the HPC layer may be cured, for example, by heating or using ultraviolet (UV) light, as is known in the art. After the coating and curing processes, additives and other functional materials not bound to the inner surface 322 may be rinsed out or otherwise removed.

Referring to FIG. 7, the loading base 404 is preferably made in whole or in part of a substantially rigid material, and includes a body 406 having a substantially flat or planar bottom support surface 408 and a top end 410. The body 406 has an outer wall 412 and an aperture 414 extending axially through substantially the center of the body. The aperture 414 is sized to receive at least a portion of the tip 32 of the delivery device 10 therein. A recess 418 extends downwardly from the top end 410 of the body 406 concentrically with the aperture 414 so as to define a support surface 420 at a spaced distance from the top end. The recess 418 has a diameter and a depth defined by the support surface 420 sufficient to receive at least a portion of the annulus section 206 of the stent 202 in a fully or almost fully expanded condition.

The outer wall 412 of the body 406 does not extend continuously around the body, but rather may be interrupted by a plurality of inwardly curved indentations 422 which divide the outer wall into a plurality of wall segments 424, only two of which are shown in FIG. 7. Although FIG. 7 depicts a loading base 404 having four indentations 422 evenly spaced around the periphery of the body 406, it is contemplated that the loading base may be provided with more or less than four such indentations. Indentations 422 facilitate the grasping of loading base 404.

The outer wall segments 424 of the body 406 do not extend all the way to the top end 410 of the body, but rather terminate at their top ends at a continuous wall 426 oriented at an oblique angle to the outer wall 412. At their bottom ends, outer wall segments 424 each include a radially projecting supporting plate 428, the bottom surfaces of which are substantially coplanar with the bottom support surface 408 of the body 406. At least one pin 430 may protrude radially outward from each outer wall segment 424. The pins 430 are preferably spaced a sufficient distance from supporting plates 428 and sized and shaped to be received in the slots 316 of the compression member 302 to join the compression member and the loading base 404 together.

When joined together, the compression member 302 and the loading base 404 collectively define a partial loading assembly.

Figure 8:
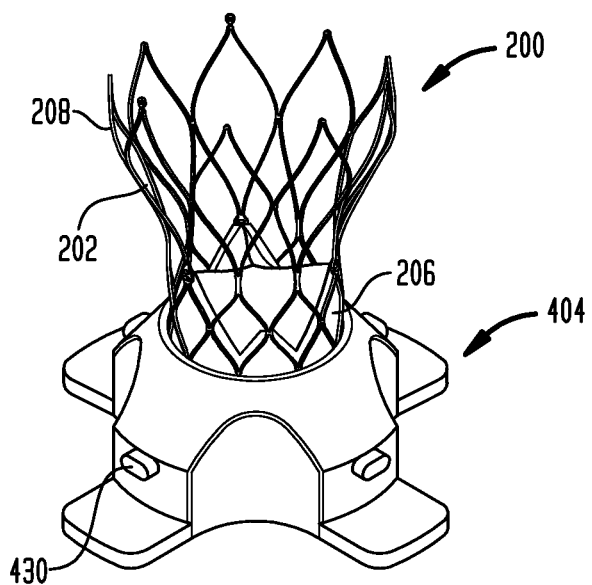
FIG. 8 illustrates the expanded prosthetic heart valve of FIG. 3 assembled onto the loading base of FIG. 7.
Figure 9:
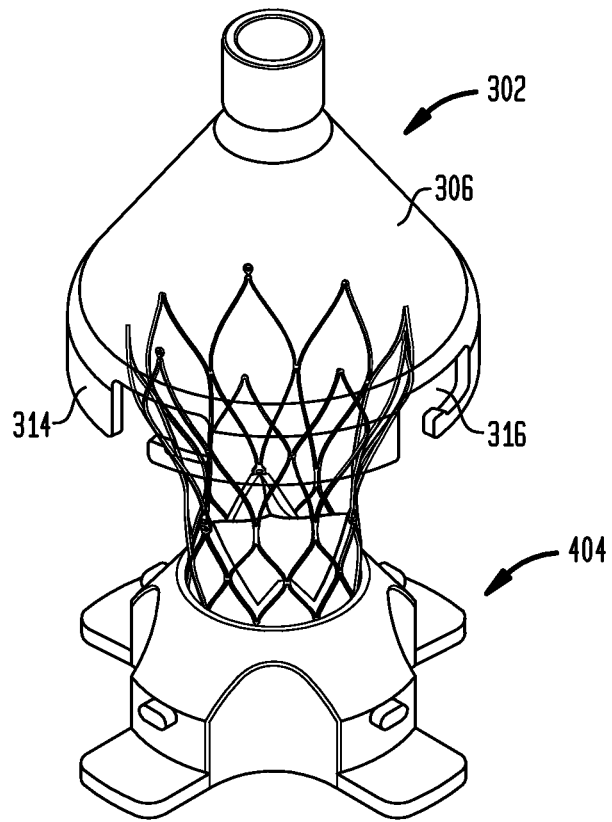
FIG. 9 illustrates the loading funnel of FIG. 5 being coupled to the loading base of FIG. 8 for collapsing the prosthetic heart valve of FIG. 8.

The loading assembly described above may be used to load the collapsible prosthetic heart valve 200 into a delivery device. As shown in FIG. 8, with the loading base 404 on a flat surface, at least a portion of the annulus section 206 of the stent 202 may be placed within the recess 418 of the loading base until the end of the stent contacts support surface 420. The compression member 302 may then be placed over the aortic section 208 of the stent 202 so that the aortic section of the stent is positioned within the funnel 306, as depicted in FIG. 9. The compression member 302 and the loading base 404 may then be pushed together, the tapered inner surface 322 of the funnel 306 gradually compressing the valve 200 until a portion of the aortic section 208 of the stent 202 is forced into and through the opening 320 of the compression member. When the portion of the aortic section 208 of the stent 202 passes through the opening 320 of the compression member 302, the retainers 218 of the stent will protrude through the opening 320 and will be positioned closely adjacent to one another. At this point, the pins 430 of the loading base 404 will be positioned within the slots 316 of the compression member 302, and the members may be locked together by rotating the loading base relative to the compression member, such that the pins 430 of the loading base slide toward the closed ends of the slots 316 of the compression member.

Figure 10:
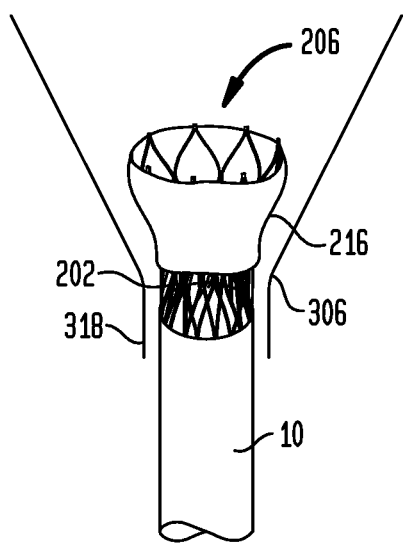
FIG. 10 illustrates schematically a delivery device coupled to the loading funnel of FIG. 5 for loading the prosthetic heart valve into the delivery device.
Figure 11:
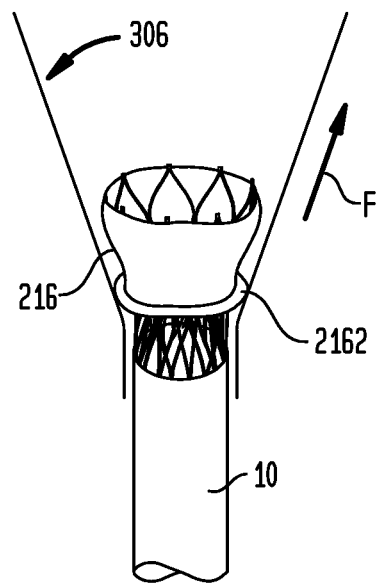
FIG. 11 illustrates schematically bunching of the outer cuff of the prosthetic heart valve of FIG. 4 within the loading funnel while the heart valve is loaded into the delivery device.
Figure 12:
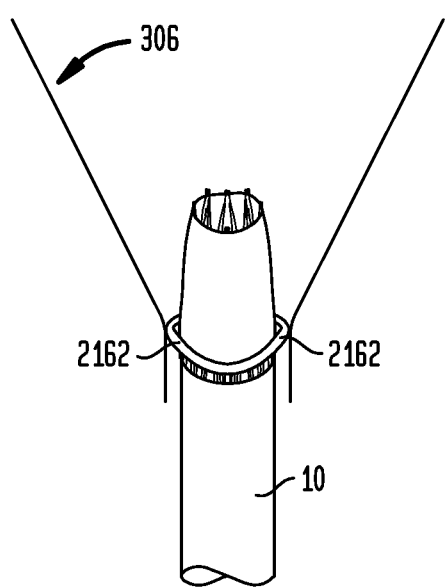
FIG. 12 schematically illustrates the bunched outer cuff of FIG. 11 engaging an edge of the delivery device.

The portion of the aortic section 208 forced into and through the opening 320 of the compression member 322 may then be received in the delivery device 10, as illustrated in FIGS. 10-12, so that the retainers 218 of the stent 202 are positioned in the pockets in retaining element 26. As the aortic section 208 of the valve 200 is pulled through the tubular extension 318, the intermediate section 210 and the annulus section 206 are gradually compressed by the tapered inner surface 322 of the funnel 306. Due to frictional resistance, designated by arrow F in FIG. 11, between the tapered inner surface 322 of the funnel 306 and the outer cuff 216, the outer cuff may start bunching up in an aggregation or roll 2162. Such frictional resistance also increases the loading force required to pull the valve 200 through the tubular extension 318 of the compression member 302 and into the delivery device 10. The roll 2162 in the outer cuff 216 may also undesirably engage the edge of the delivery device 10 as shown in FIG. 12. In one configuration, the HPC layer 324 on the inner surface 322 of the funnel 306 reduces the frictional resistance between the outer cuff 216 and the inner surface 322, thereby reducing the loading force required to the load the valve 200 into the delivery device.

Figure 13A:
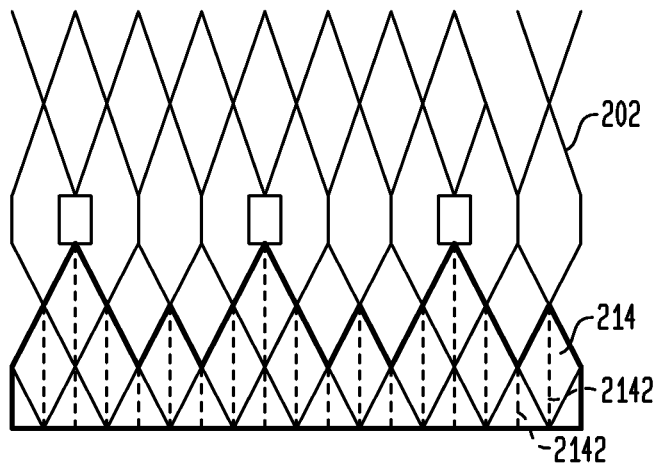
FIG. 13A is a schematic developed view of the stent and inner cuff of a prosthetic heart valve according to an embodiment of the disclosure, illustrating a folding pattern for the inner cuff.
Figure 13B:
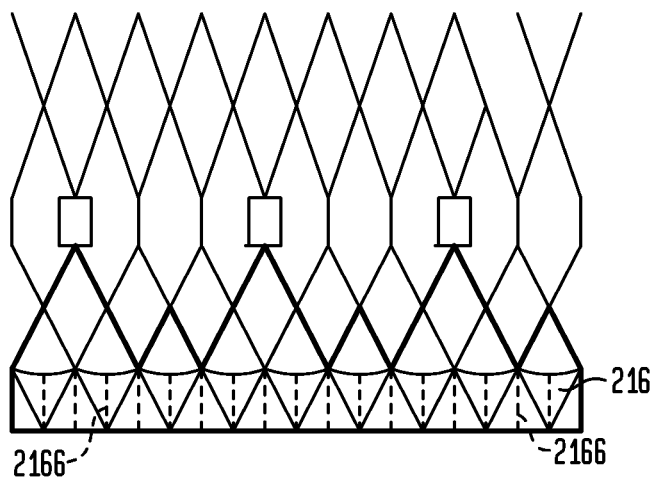
FIG. 13B is a schematic developed view of the stent and outer cuff of a prosthetic heart valve according to an embodiment of the disclosure, illustrating a folding pattern for the outer cuff.
Figure 13C:
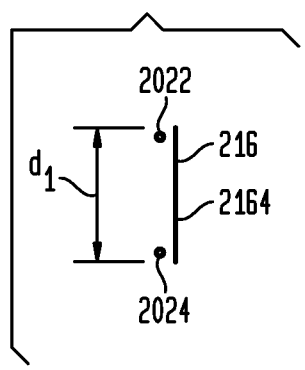
FIG. 13C is a schematic partial transverse cross-section of the stent and outer cuff in an expanded condition.
Figure 13D:
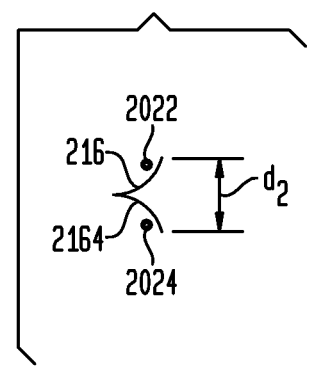
FIG. 13D is a schematic partial transverse cross-section of the stent and outer cuff of FIG. 13C in a collapsed condition.

While the stent 202 is collapsing, the inner cuff 214 may fold in such a manner as to protrude away, i.e., radially outwardly, from the stent, thereby increasing the undesirable bunching up of the cuff material and/or the engagement of the cuff material with the edge of the delivery device 10. To prevent such an occurrence, in an embodiment, the fabric of the inner cuff 214 may be pre-folded at least partially, such that when the stent 202 is collapsing, the inner cuff will tend to fold toward the interior, i.e., radially inwardly, of the stent 202. In an exemplary embodiment illustrated in FIG. 13A, the fabric of the inner cuff 214 has fold lines 2142 along which the fabric preferably folds. The fold lines 2142 may be formed by applying heat, for example, by ironing the fabric in a folded condition in which the fold lines face toward the radial center of the stent 202. In another example, the fold lines 2142 may be formed by applying force and folding the fabric prior to attaching the inner cuff 214 to the stent 202. Likewise, the fabric of the outer cuff 216 may be pre-folded to form fold lines 2166, as illustrated in FIGS. 13B-D, such that when the stent 202 is collapsing, the fabric of the outer cuff 216 will tend to fold radially inward between the struts of the stent. The fold lines 2166 may be formed in the same manner or manners as the fold lines 2142.

FIG. 13C illustrates, in partial transverse cross-section, two adjacent struts 2022, 2024 of the stent 202 at a first distance d1 from one another when the stent is in an expanded condition, and a segment 2164 of the fabric of the outer cuff 216 on the exterior of the stent. When the stent 202 is collapsing, the adjacent struts 2022, 2024 move closer to one another so that there is a distance d2 between them, the distance d2 being smaller than the distance d1. The fabric segment 2164 folds between adjacent struts 2022, 2024 toward the interior of the stent 202, i.e., radially inwardly. Such a folding pattern for the outer cuff 216 may prevent or reduce the formation of the roll 2162.

Figure 14A:
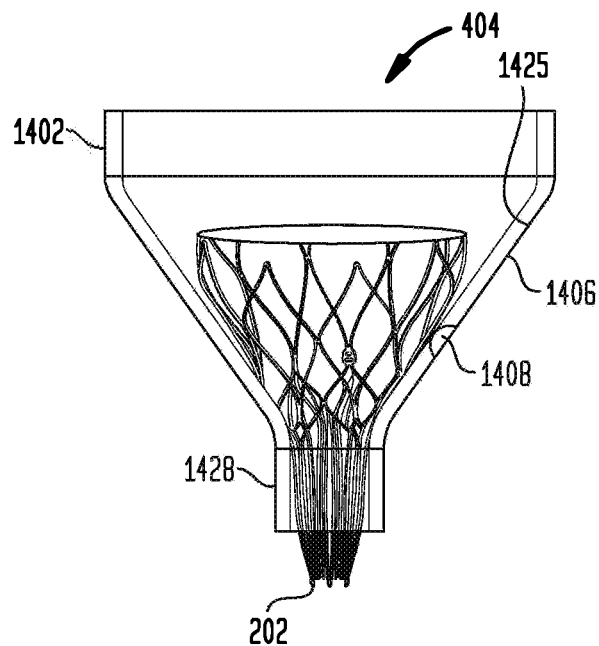
FIG. 14A is a longitudinal cross-section of another embodiment of a loading funnel with a plurality of ridges defined on an inner surface of the tapered wall thereof.
Figure 14B:
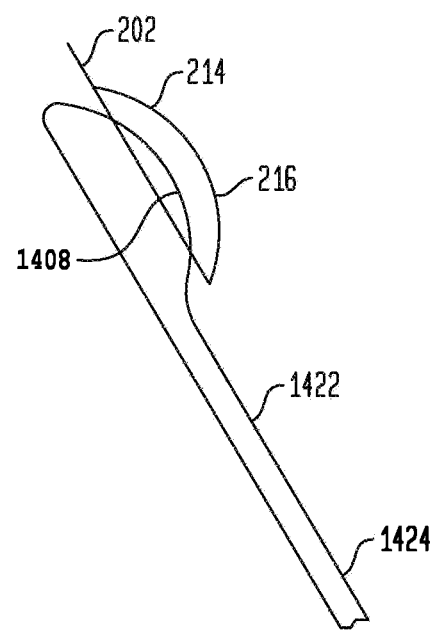
FIG. 14B is a schematic longitudinal cross-section of a portion of the loading funnel of FIG. 14A.

In addition, or as an alternative, to the pre-folding of the fabrics of the inner cuff 214 and the outer cuff 216, one or more components of the loading assembly may be configured to cause the fabrics of the inner cuff and the outer cuff to fold radially inwardly. For instance, in an embodiment illustrated in FIGS. 14A-14B, the funnel 1406 of the compression member 1402 may include a plurality of protrusions 1408 defined on its inner surface 1425. As the valve 200 is pulled through the tubular extension 1428 of the compression member 1402 and the stent 202 is collapsing, the plurality of protrusions 1408 urge the fabrics of the outer cuff 216 and the inner cuff 214 radially inwardly between adjacent struts of the stent and into the stent interior. As the fabric of the outer cuff 216 is pushed radially inwardly by the plurality of protrusions 1408, the aggregation or rolling of the fabric, such as the formation of roll 2162, may be avoided. In one example, the compression member 1402 may include an HPC layer 1424 on its inner surface 1422. The HPC layer 1424 may be similar to the HPC layer 324 described above, and may contribute to preventing the undesirable aggregation or rolling of the fabric of the outer cuff 216.

The plurality of protrusions 1408 may be placed circumferentially on the inner surface 1425 of the funnel 1406. In an example, the protrusions 1408 may be uniformly spaced apart from one another. For example, the spacing between two adjacent protrusions 1408 may be between about 0.05 inches (in.) and about 0.25 in. Preferably, the spacing between the protrusions 1408 is such that the protrusions align with the center of the stent cells in an expanded condition of the stent, enabling the protrusions to push the fabrics of the inner cuff 214 and the outer cuff 216 through the stent cells to the interior of the stent. The protrusions 1408 may have a length between about 0.05 in. and about 0.5 in., a thickness from the inner surface 1425 between about 0.02 in. and about 0.1 in., and a width between about 0.02 in. and about 0.05 in. In an exemplary embodiment, all of the protrusions 1408 may be uniformly dimensioned. In another embodiment, the dimensions of the protrusions 1408 may vary. For instance, one of the protrusions 1408 may have a first set of dimensions, while protrusions adjacent to the one protrusion may have at least one dimension that differs from the first set. Such a configuration may aid in the folding of the inner cuff 214 and the outer cuff 216 within the stent cells of different sizes or locations within the stent. In yet another embodiment, a first subset of the protrusions 1408 may have a first set of dimensions, while subsets of protrusions 1408 adjacent the first subset may have at least one dimension that is different from those of the first set.

The plurality of protrusions 1408 may be formed integrally with the compression member 1402, for example, using injection molding techniques. Alternatively, the protrusions 1408 may be formed separately from the compression member, and may be assembled to the inner surface 1425 of the funnel 1406 by any known technique, including a snap or press fit arrangement, fasteners, adhesive, ultrasonic welding and the like.

In one embodiment, the plurality of protrusions 1408 may be provided at about a longitudinal mid-point of the inner surface 1425 of the funnel 1406. In another embodiment, the plurality of protrusions 1408 may be provided proximate the tubular extension 1428. In yet another embodiment, the funnel 1406 may include a first series of protrusions 1408 at about the longitudinal mid-point of the inner surface 1425 of the funnel 1406 and a second series of ridges 1408 proximate the tubular extension 1428. The first and second series of ridges 1408 may alternate around the circumference of the funnel 1406.

Referring now to FIGS. 15A-15F, a further embodiment of a loading assembly is described. The loading assembly includes a loading base 1500, a base funnel or a first compression member 1600 and a loading funnel or a second compression member 1402 that may be similar to the compression members 302 or 1402 described above. The loading base 1500 may be generally similar to the loading base 404 with a few differences. For instance, the recess 418 of the loading base 404 is generally sized to receive the annulus section 206 of the valve 200 in a fully expanded condition. In contrast, the loading base 1500 includes a recess 1518 having a size smaller than the size of a fully expanded annulus section 206 of the heart valve 200. More particularly, the recess 1518 has an inner diameter $d_r$ smaller than the diameter of the fully expanded annulus section 206, such that the recess receives the annulus section of the valve 200 in an at least partially collapsed condition. In an example, the inner diameter $d_r$ may be about 50% of the diameter of the fully expanded annulus section 206. The recess 1518 of the loading base 1500 is configured to receive a substantial portion of the annulus section 206 of the valve 200. To accommodate the annulus section 206, the recess 1518 has a height $h_r$ almost corresponding to the height of the annulus section. In an example, the recess 1518 of the loading base 1500 may have a height sufficient to receive from about 70% to about 90% of the height of the annulus section 206. Thus, when the annulus section 206 of the valve 200 is received in the loading base 1500, the stent 202 is at least partially collapsed and, as described in detail below, the fabrics of the inner cuff 214 and the outer cuff 216 are folded inwardly into the stent 206.

Figure 15A:
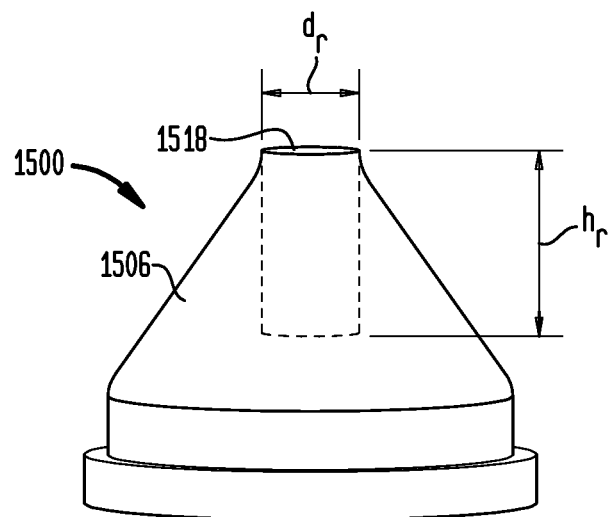
FIG. 15A is a perspective view of another embodiment of a loading base.
Figure 15B:
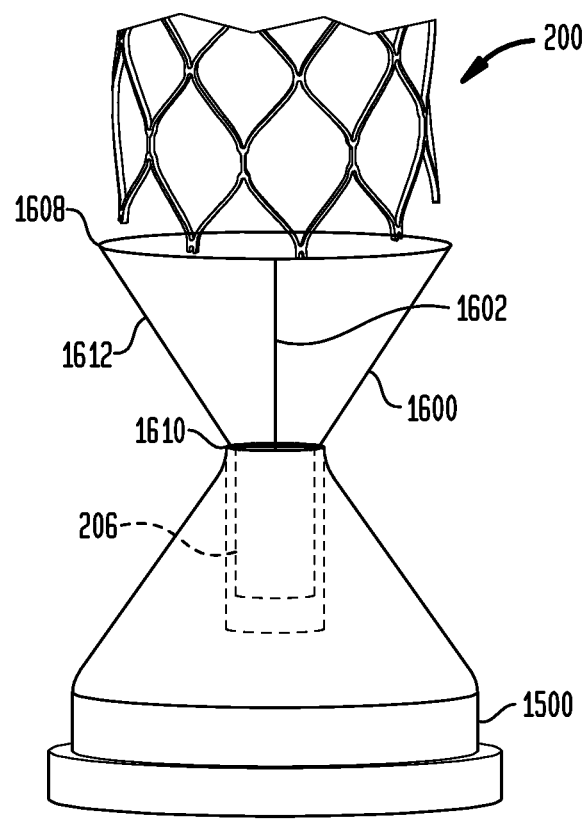
FIG. 15B illustrates an embodiment of a base funnel coupled to the loading base of FIG. 15A for loading a prosthetic heart valve into the loading base.

The base funnel 1600 is configured to be coupled to the loading base 1500 for inserting the annulus section 206 of the heart valve 200 into the recess 1518 of the loading base 1500, as shown in FIG. 15B. The base funnel 1600 has a first open end 1608, a second open end 1610 and a tapered wall 1612 extending between the first and second open ends. The first end 1608 of the base funnel 1600 has a diameter sized to receive the annulus section 206 of the valve 200 in a fully expanded condition. The second end 1610 of the base funnel 1600 has a diameter that is slightly smaller than or the same as the diameter of the recess 1518, i.e., the outer diameter of the second end 1610 is slightly smaller than or the same as the inner diameter $d_r$. The base funnel 1600 may be coupled to the loading base 1500 in a variety of ways, such as a snap fit, a press fit, or a screw mechanism. With the base funnel 1600 coupled to the loading base 1500, the annulus section 206 of the heart valve 200 may be pushed through the base funnel, as shown in FIG. 15D, whereupon the annulus section at least partially collapses and is received in recess 1518. As the stent 202 is partially collapsed in the annulus section 206, the fabrics of the inner cuff 214 and the outer cuff 216 may be folded inwardly between the struts of the stent. In an exemplary embodiment, the base funnel 1600 is configured with a longitudinal split 1602, shown in FIG. 15C, that enables two portions of the base funnel to be moved relative to one another. After the annulus section 206 has been inserted through the base funnel 1600 and into the recess 1518, the portions of the base funnel may be opened up along the split 1602 and removed from the loading base 1500, as shown in FIG. 15E. In another embodiment, the base funnel 1600 may have two longitudinal splits 1602 diametrically opposite one another such that the two portions of the base funnel may be completely separated from one another.

Figure 15C:
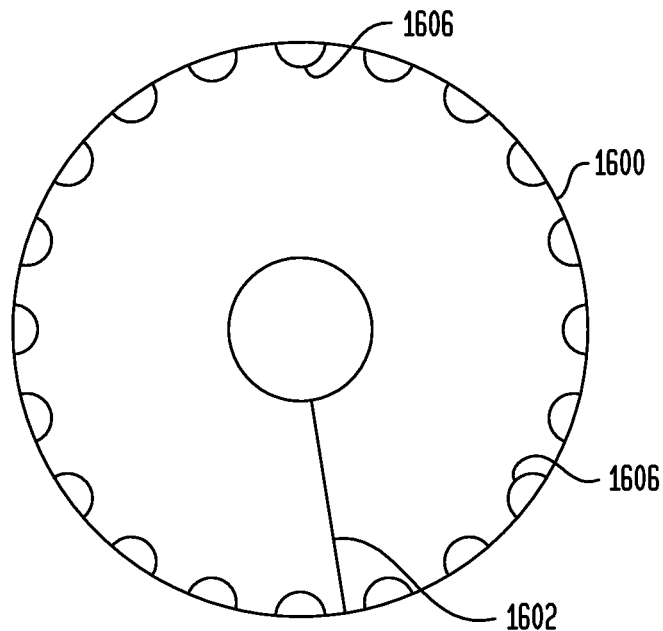
FIG. 15C schematically illustrates a top view of the base funnel of FIG. 15B.
Figure 15D:
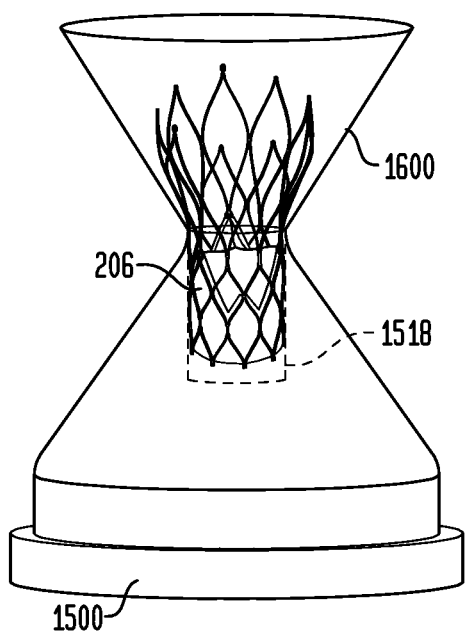
FIGS. 15D-E are front perspective views showing a process of loading the prosthetic heart valve into the loading base of FIG. 15A using the base funnel of FIG. 15B.
Figure 15E:
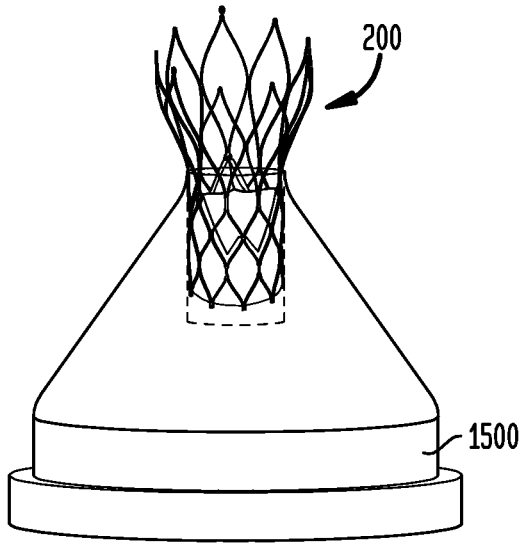
Figure 16A:
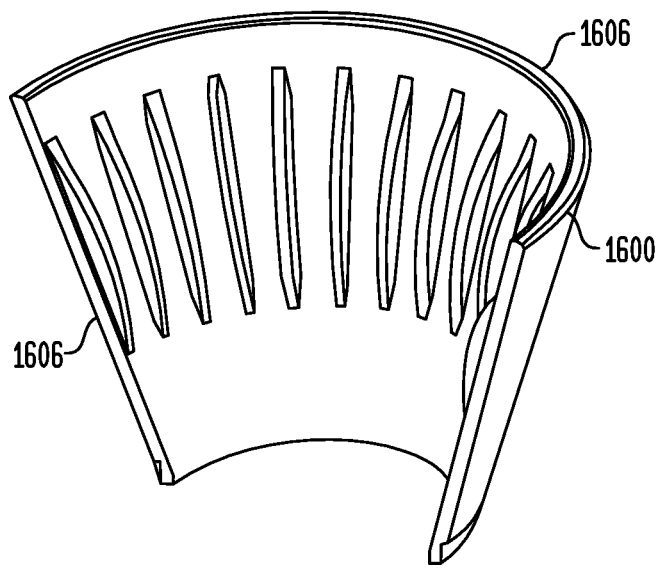
FIG. 16A is a partial perspective view of an embodiment of the base funnel with ridges.
Figure 16B:
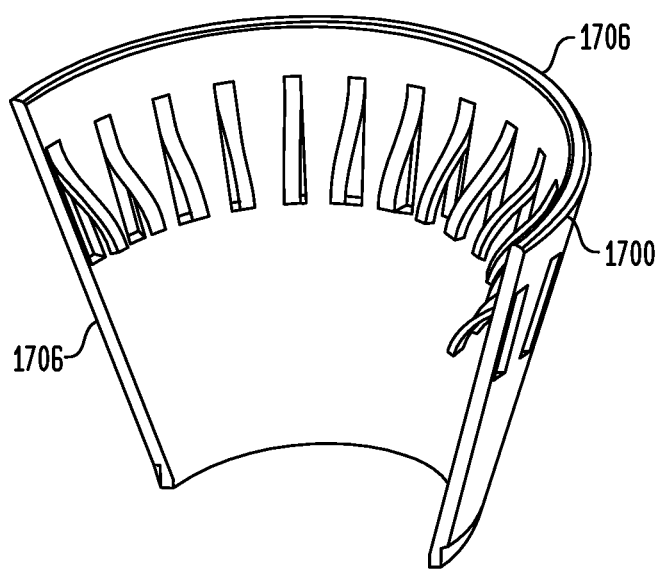
FIG. 16B is a partial perspective view of an embodiment of the base funnel with spring-like fingers.

The base funnel 1600 may include a plurality of ridges 1606 as shown in FIGS. 15C, 16A. Ridges 1606 may be similar to the protrusions 1408 described above, and are configured to urge the fabrics of the inner cuff 214 and the outer cuff 216 to fold radially inwardly into the interior of the stent 202. In another embodiment, illustrated in FIG. 16B, a base funnel 1700 may include a plurality of spring-like fingers 1706 that protrude inwardly from the tapered wall of the base funnel. The spring-like fingers 1706 are configured to urge the fabrics of the inner cuff 214 and the outer cuff 216 radially inwardly into the interior of the stent 202, between adjacent struts thereof, in a manner similar to that of the ridges 1606. However, if one or more struts of the stent 202 engage a spring-like finger 1706, the finger will yield to the strut and get pushed radially outwardly toward and into the tapered wall of the funnel 1700. As a result, damage to the stent 202 may be prevented or minimized.

Figure 15F:
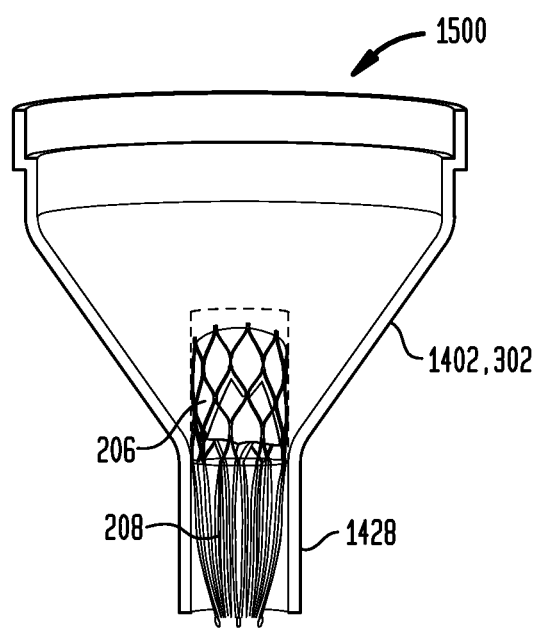
FIG. 15F is a longitudinal cross-section showing a compression member coupled to the loading base of FIG. 15A and to a delivery device for loading the prosthetic heart valve into the delivery device.

FIG. 15F shows the loading base 1500 in an inverted orientation and coupled to a compression member 302, 1402 for loading the valve 200 into the delivery device 10 as described above. More particularly, the second open end of the compression member 1402 is placed over the loading base 1500 and over the aortic section 208 of at least partially collapsed heart valve 200. The at least partially collapsed annulus section 206 of the heart valve 200 resides in the recess 1518, whereas the aortic section 208 faces the tubular extension 1428 of the compression member 1402. As the compression member 1402 is moved closer to the loading base 1500, the compression member begins to compress the aortic section 208. The compressed aortic section 208 is then pulled through the tubular extension 1428, thereby further compressing the heart valve 200. As the annulus section 206 engages the compression member 1402, it may be further compressed, if it is not completely compressed in the recess 1518. This additional compression may be achieved by forming the tubular extension 1428 with an inner diameter that is smaller than the inner diameter $d_r$ of the recess 1518. Since the annulus section 206 of the valve 200 is at least partially collapsed with the fabrics of the inner cuff 214 and the outer cuff 216 folded inwardly, formation of a fabric bunch or roll, such as roll 2162, may be prevented. The aortic section 208 and the annulus section 206 are compressed tightly as they pass through the tubular extension 1428 and the compressed heart valve 200 may then be loaded into the delivery device 10.

FIG. 17 illustrates a flow chart of a method for loading the heart valve 200 into the delivery device 10 using the loading base 1500, the base funnel 1600 and the compression member 1402. At step 1810, the base funnel 1600 is coupled to the loading base 1500 such that the second open end 1610 of the base funnel is received within with the recess 1518 of the loading base. At step 1820, the annulus section 206 of the heart valve 200 is inserted into the base funnel 1600. As the heart valve 200 is pushed into the base funnel 1600, the annulus section 206 is at least partially collapsed by the tapered inner surface of the base funnel until it passes through the narrow second open end 1610 and is received within the recess 1518 of the loading base 1500. After the annulus section 206 has been received in the recess 1518, the base funnel 1600 is removed from the loading base 1500, at step 1830, leaving the heart valve 200 in the loading base 1500. At step 1840, the compression member 1402 is coupled to the loading base 1500 with the aortic section 208 of the heart valve 200 facing the tubular extension 1428. The coupling of the compression member 1402 to the loading base 1500 further collapses the heart valve 200, particularly at its aortic section 208. The heart valve 200 is then loaded into the delivery device 10 as described above with reference to FIGS. 9 and 10. Since the annulus section 206 of the heart valve 200 is at least partially collapsed, the fabrics of the inner cuff 214 and the outer cuff 216 are held between the adjacent struts 202 and do not interfere or create resistance when the heart valve is loaded into the delivery device 10.

To summarize the foregoing, a first aspect of the disclosure describes a compression member for collapsing a prosthetic heart valve. The compression member includes:

a first open end with a first diameter;

a second open end with a second diameter less than the first diameter;

a tapered wall decreasing in diameter from the first open end to the second open end and having an inner surface, the tapered wall defining an open space adapted to receive the prosthetic heart valve; and a plurality of protrusions on the inner surface of the tapered wall, the protrusions being adapted to urge portions of an outer cuff of the prosthetic heart valve to an interior of the valve as the valve moves from the first open end toward the second open end; and/or the inner surface may include a layer of a hydrophilic coating; and/or each of the protrusions is a spring-like finger; and/or each of the spring-like fingers is deflectable toward the inner surface; and/or the inner surface includes a layer of a hydrophilic coating.

A second aspect of the disclosure describes a system for collapsing a prosthetic heart valve. The system includes:

a loading base having a body and a recess formed in the body, the recess having a support surface and being configured to receive an annulus section of a prosthetic valve in an at least partially collapsed condition;

a first compression member having a first open end with a first diameter, a second open end with a second diameter less than the first diameter, and a tapered wall decreasing in diameter from the first open end to the second open end, the first compression member being configured to be positioned against the loading base, to receive the annulus section of the prosthetic valve in an expanded condition and to collapse the annulus section of the prosthetic valve to the at least partially collapsed condition; and a second compression member having a first open end with a third diameter, a tubular extension at the first open end, a second open end with a fourth diameter larger than the third diameter, and a tapered wall decreasing in diameter from the second open end to the tubular extension, the second compression member being configured to be positioned against the loading base at the second open end and to collapse an aortic section and the at least partially collapsed annulus section of the prosthetic valve; and/or a prosthetic heart valve having an expanded condition, a collapsed condition, a stent formed of a plurality of struts, an inner cuff and an outer cuff, a fabric of at least one of the inner cuff and the outer cuff in the expanded condition of the prosthetic heart valve having fold lines such that when the prosthetic heart valve is moved to the collapsed condition, the fabric is folded along the fold lines radially inwardly between adjacent ones of the struts into an interior of the stent; and/or at least one of the first compression member and the second compression member includes a layer of a hydrophilic coating on an inner surface thereof; and/or the tapered wall of at least one of the first compression member and the second compression member includes a plurality of protrusions extending radially inwardly, the plurality of protrusions being configured to urge portions of an outer cuff of the prosthetic heart valve to the interior of the valve; and/or each of the protrusions is a spring-like finger; and/or the first compression member includes a split extending from the first open end to the second open end, the split enabling two portions of the first compression member to be moved relative to one another.

A third aspect of the disclosure describes a method for loading a prosthetic heart valve into a delivery device. The method comprises:

at least partially collapsing an annulus section of the prosthetic heart valve by inserting through an orifice;

positioning the at least partially collapsed annulus section in a loading base;

collapsing an aortic section of the prosthetic heart valve; and loading the collapsed aortic section into the delivery device; and/or further collapsing the annulus section to load the prosthetic heart valve into the delivery device; and/or the step of at least partially collapsing the annulus section of the prosthetic heart valve includes positioning a first compression member against the loading base and passing the annulus section of the prosthetic heart valve through the first compression member; and/or moving the first compression member away from the loading base after positioning the at least partially collapsed annulus section in the loading base; and/or the step of collapsing the aortic section of the prosthetic heart valve includes positioning a second compression member against the loading base and passing the aortic section of the prosthetic heart valve through the second compression member; and/or the loading step includes loading the prosthetic heart valve into the delivery device through the second compression member.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for loading a prosthetic heart valve into a delivery device, the method comprising:
   positioning a first compression member having an orifice against a loading base;
   inserting an annulus section of the prosthetic heart valve through the first compression member and through the orifice so as to at least partially collapse the annulus section of the prosthetic valve;
   positioning the at least partially collapsed annulus section in the loading base;
   at least partially collapsing an aortic section of the prosthetic heart valve while the at least partially collapsed annulus section is in the loading base; and
   loading the prosthetic heart valve into the delivery device by loading the at least partially collapsed aortic section into the delivery device without passing the prosthetic heart valve through the loading base.

2. The method according to claim 1, further comprising further collapsing the partially collapsed aortic section prior to loading the prosthetic heart valve into the delivery device.

3. The method according to claim 1, further comprising moving the first compression member away from the loading base after positioning the at least partially collapsed annulus section in the loading base.

4. The method according to claim 1, wherein the step of at least partially collapsing the aortic section includes positioning a second compression member against the loading base and over the partially collapsed aortic section so as to pass the at least partially collapsed aortic section through the second compression member.

5. The method according to claim 4, wherein the loading step includes loading the prosthetic heart valve into the delivery device through the second compression member.

6. The method according to claim 1, further comprising removing the first compression member before at least partially collapsing an aortic section of the prosthetic heart valve.

7. The method according to claim 1, wherein the first compression member includes a plurality of ridges configured to urge fabrics of an inner cuff of the prosthetic heart valve to fold radially inward when the annulus section of the prosthetic heart valve is inserted through the first compression member.

8. The method according to claim 1, wherein the first compression member includes a plurality of springlike fingers configured to urge fabrics of an inner cuff of the prosthetic heart valve to fold radially inward when the annulus section of the prosthetic heart valve is inserted through the first compression member.

* * * * *